(12) United States Patent
Kolb et al.

(10) Patent No.: US 9,345,792 B2
(45) Date of Patent: May 24, 2016

(54) FORMULATION, APPARATUS AND METHOD FOR STABILIZING RADIOPHARMACEUTICALS

(75) Inventors: Hartmuth C. Kolb, Playa del Rey, CA (US); Joseph C. Walsh, Pacific Palisades, CA (US); Vani P. Mocharla, Los Angeles, CA (US); Fanrong Mu, South Pasadena, CA (US); Umesh B. Gangadharmath, Los Angeles, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 250 days.

(21) Appl. No.: 13/813,687

(22) PCT Filed: Aug. 15, 2011

(86) PCT No.: PCT/US2011/047717
§ 371 (c)(1),
(2), (4) Date: Apr. 2, 2013

(87) PCT Pub. No.: WO2012/021882
PCT Pub. Date: Feb. 16, 2012

(65) Prior Publication Data
US 2013/0183238 A1 Jul. 18, 2013

Related U.S. Application Data

(60) Provisional application No. 61/373,321, filed on Aug. 13, 2010, provisional application No. 61/392,583, filed on Oct. 13, 2010.

(51) Int. Cl.
*A61K 51/04* (2006.01)
*A61K 51/12* (2006.01)
*A61K 9/00* (2006.01)
*A61K 47/12* (2006.01)

(52) U.S. Cl.
CPC ......... *A61K 51/0402* (2013.01); *A61K 51/0459* (2013.01); *A61K 51/121* (2013.01); *A61K 51/1282* (2013.01); *A61K 9/0019* (2013.01); *A61K 47/12* (2013.01)

(58) Field of Classification Search
None
See application file for complete search history.

(56) References Cited

FOREIGN PATENT DOCUMENTS

EP 1 356 827 A1 10/2003
WO 2009/059977 A1 5/2009

OTHER PUBLICATIONS

"List of Radiopharmaceuticals", retrieved from http://nuclearpharmacy.uams.edu/RPLIST.html on Mar. 4, 2015.*
Berger et al., "Radical scavengers and the stability of <99m>Tc-radiopharmaceuticals", International Journal of Applied Radiation and Isotops, vol. 33, pp. 1341 to 1344, 1982.
Mark S Jacobson, et al., "Radiolysis of 2-[18F]fluoro-2-deoxy-d-glucose ([18F]FDG) and the role of ethanol and radioactive concentration", Applied Radiation and Isotopes, vol. 67, No. 6, Jun. 1, 2009, pp. 990-995.

(Continued)

*Primary Examiner* — Ernst V Arnold
*Assistant Examiner* — Jianfeng Song
(74) *Attorney, Agent, or Firm* — Peter Kendall

(57) ABSTRACT

A formulation for stabilizing a radiopharmaceutical. The formulation includes a radiopharmaceutical (or a pharmaceutically acceptable salt thereof), a gas which has oxygen, a stabilizer, and a solvent.

4 Claims, 6 Drawing Sheets

(56) References Cited

OTHER PUBLICATIONS

Peter J.H. Scott, et al., "Studies into radiolytic decomposition of fluorine-18 labeled radiopharmaceuticals for positron emission tomography", Applied Radiation and Isotopes, vol. 67, No. 1, Jan. 1, 2009, pp. 88-94.

Search report dated Jun. 29, 2012 of International Application Serial No. PCT/US2011/047717.

* cited by examiner

FORMULATION, APPARATUS AND METHOD FOR STABILIZING RADIOPHARMACEUTICALS

This application is the U.S. national phase application of PCT International Application No. PCT/US2011/047717, filed on Aug. 15, 2011, which claims priority to Provisional U.S. Patent Application Nos. 61/392,583, filed Oct. 13, 2010, and 61/373,321, filed Aug. 13, 2010, the disclosures of which are incorporated herein by reference in their entirety.

BACKGROUND OF THE INVENTION

1. Field of the Invention

The present invention relates to positron emission tomography (PET). More specifically, it relates to radiopharmaceuticals used in PET. More particularly, it relates to formulations and methods for stabilizing these radiopharmaceuticals. These formulations and methods prevent these radiopharmaceuticals from degrading due to many factors including radiolysis.

2. Description of Related Art

Over the past 10 years positron emission tomography (PET) has evolved from a research tool to a commonly applied clinical diagnostic test. At the heart of PET imaging are isotope-labeled radiopharmaceuticals that undergo specific biological transformations (e.g. enzymatic transformation, such as phosphorylation) or bind to biomolecules with high specificity and affinity. PET imaging not only enables disease diagnosis in a clinical setting, but also supports the development of new therapeutic drugs by allowing receptor occupancy and pharmacokinetic properties to be evaluated in vivo.

The formulation and stabilization of radiopharmaceuticals for PET imaging is a critical component to the manufacturing process. Radiopharmaceuticals must be formulated appropriately for human dosing; the most common delivery route being intravenous administration of aqueous solutions. At a minimum, the formulation must not adversely compromise the stability of the radiopharmaceutical for the duration of its shelf-life. In an ideal scenario, the formulation provides an extra measure of protection against radiopharmaceutical degradation. This aspect of stability is critical since bulk dose vials containing radiopharmaceutical are often made in high strength (mCi/mL) to enable dispensing of multiple doses over a period of several hours. In addition, it is critical to maintain a high radiochemical purity to achieve the best image quality possible. If the stability of the bulk vial is compromised during the duration of its shelf-life, the dose may be unusable and unfit for human dosing or imaging.

Radiopharmaceuticals can experience instability as a function of strength (mCi/mL), pH, temperature and specific activity. One of the major issues with respect to radiopharmaceutical formulations is radiolysis (i.e. radiolytic degradation), which can occur while the radiopharmaceutical is aging in the dosing solution or bulk vial. The radiolysis process is not fully understood but current research suggests that ionizing radiation, generated via positron decay, induces the formation of radicals. See Jan Van Den Bos, (Healthcare, G., Ed.) (2009) (related to WO 2009/059977); Maxim Y. Kiselev et al., (Isotopes, E., Ed.) (2004) (related to WO 2004/043497; Jianqing Chen et al., (S.P.A., B. I., Ed.) (2005) (related to WO 2005/009393); Richard M. Fawdry, *Radiolysis of 2-[18F]fluoro-2-deoxy-D-glucose (FDG) and the Role of Reductant Stabilizers*, Applied Radiation and Isotopes, vol. 65, pp. 1193-1201 (2007).

For example, one reference describes radiolysis as being "caused mainly by oxidation by free radicals that are produced by the interaction of ionizing radiation from the $^{18}$F-isotope with the water solvent and possibly air". Maxim Y. Kiselev et al. (Isotopes, E., Ed.) (2004). Another reference cites that "the interaction of ionizing radiation with dissolved oxygen ($O_2$) can generate very reactive species such as superoxide radicals. These radicals are very reactive towards organic molecules". Jianqing Chen et al. (S.P.A., B. I., Ed.) (2005). As a consequence of the formation of these radicals, they can react further with each other, other radicals, oxygen and/or the radiopharmaceutical itself eventually causing radiolytic decomposition of the radiopharmaceutical.

Experiments using ionizing radiation on solutions of thymidine demonstrate the destructive effects caused by the decomposition products that react with thymidine. See J. R. Wagner et al., *Photo and Radiation-Induced Formation of Thymidine Hydroperoxides*, Bioelectrochemistry and Bioenergetics, vol. 18, pp. 155-162 (1987); R. Teoule & J. Cadet, *Comparison of Radiolysis Products of Thymine and Thymidine with E.S.R. Results*, Int'l J. Radiation Biology, vol. 27, pp. 211-222 (1975). The effects are further exacerbated by the presence of oxygen and often lead to peroxide-containing adducts. While these reports utilize an external source of radiation, the proposed decomposition adducts react with thymidine in a fashion consistent with radiolysis. For example, the author states the following:

"The formation of hydroperoxides during gamma radiolysis of dThd in oxygenated solutions most likely under these conditions involves the initial reactions of hydroxyl radicals with dThd. Hydroxyl radicals react with dThd by addition to the 5,6 double bond and by hydrogen abstraction either from the sugar moiety or from the methyl group."

See J. R. Wagner et al., *Photo and Radiation-Induced Formation of Thymidine Hydroperoxides*, Bioelectrochemistry and Bioenergetics, vol. 18, pp. 155-162 (1987).

It is clear that ionization radiation, albeit from an external source, can lead to radiolysis on non-radioactive species, especially in the presence of air (oxygen).

The byproducts from the radiolysis-induced radical reactions are believed to be strongly oxidizing. For example, if hydroxyl radical is formed during radiolysis, it may combine with another hydroxyl radical to form hydrogen peroxide, a strong oxidizer. In another example, it is widely believed that ionizing radiation in the presence of oxygen leads to the formation of superoxide, a highly oxidizing and reactive species, which rapidly degrades radiopharmaceuticals. In an effort to combat the negative effect of these radicals in a strongly oxidizing environment, stabilizers are often added to the dosing solution. More specifically, these stabilizers are comprised of radical scavengers and/or anti-oxidants (i.e. reductants), both of which are believed to exert a protective effect upon the radiopharmaceutical against radiolysis. The effect of reductants on the inhibition of [F-18]FDG radiolysis is well studied in the art. See Richard M. Fawdry, *Radiolysis of 2-[18F]fluoro-2-deoxy-D-glucose (FDG) and the Role of Reductant Stabilizers*, Applied Radiation and Isotopes, vol. 65, pp. 1193-1201 (2007).

Table 1 shows some commonly-used tracers and stabilizers commonly-used with these tracers.

TABLE 1

Common stabilizers for [F-18]-labeled radiopharmaceuticals

| Stabilizer | Tracer | Reference |
|---|---|---|
| Ethanol | [F-18]FDG | WO2004043497 |
| N-t-butyl-alpha-phenylnitrone (PBN) | [F-18]AV-19 | Appl. Radiat. Isot. 2009, 67, 88-94 |
| Sodium ascorbate | [F-18]AV-19 | Appl. Radiat. Isot. 2009, 67, 88-94 |
| Ascorbic acid | [F-18]AV-45 | WO2010078370 |
| Ascorbic acid | [F-18]FDDNP | Appl. Radiat. Isot. 2008, 66, 203-207 |
| Gentisic acid | [F-18]FDG | WO2009059977 |
| Calcium chloride | 2-[F-18]fluoromethyl-L-phenylalanine | Nucl. Med. Biol. 2008, 35(4), 425-432 |

Consistent with the thinking that oxidation plays a negative role in radiopharmaceutical stabilization; oxidants are not used to stabilize radiopharmaceuticals. Oxidants are expected to contribute to further radical growth, and thus increase the propensity for radiolysis. One reference discloses that stabilized radiopharmaceutical compositions are defined as those which are preferably stored in an environment from which oxygen gas has been removed. Jan Van Den Bos, (Healthcare, G., Ed.) (2009).

The above stabilizers are used in formulations that are devoid of oxygen. Since the stabilizers are largely anti-oxidants, using them to stabilize radiopharmaceuticals in the presence of oxygen would be expected to lessen their protective effect. For example, ascorbic acid rapidly degrades in the presence of oxygen, often changing color as a result of this degradation. The rapid decay of these stabilizers in air also means that solutions containing these stabilizers cannot be stored for long periods of time.

Accordingly, if oxygen was found to have a protective effect against radiolysis, then the addition of oxygen and certain non-oxidizing excipients into radiopharmaceutical formulations may have a synergistic effect that could not be accomplished through the use of either oxygen or the excipient alone. For example, if a non-oxidizing excipient such as maleic acid (MA) exerted a stabilizing effect on radiopharmaceuticals in the absence of oxygen, MA's protective effect on the radiopharmaceutical stability profile could be substantially increased in the presence of oxygen.

Maleic acid (MA) is a dicarboxylic acid that is a common excipient in non-radioactive injectable formulations. Its toxicity profile is well known. Int'l J. Toxicology, Am. C. *Toxicology, Final Report on the Safety Assessment of Maleic Acid*, vol. 26, suppl. 2, pp. 125-130 (2007). It is listed as an inactive ingredient for injection by the United States Food and Drug Administration (FDA) with a maximum potency of 0.01%.

MA causes a reversible malfunctioning of the proximal renal tubes in kidneys by forcing materials intended for re-absorption (glucose, $HCO_3^-$, etc.) to be excreted into the urine. Somchai Eiam-ong et al., *Insights Into the Biochemical Mechanism of Maleic Acid-Induced Fanconi Syndrome*, Kidney Int'l, vol. 48, pp. 1542-1548 (1995); Edgar J. Rolleman et al., *Kidney Protection During Peptide Receptor Radionuclide Therapy with Somatostatin Analogues*, Eur. J. Nuclear Med. & Molecular Imaging, vol. 37, pp. 1018-1031 (2010); Salim K. Mujais, "*Maleic Acid-Induced Proximal Tubulopathy: Na:K Pump Inhibition*", J. Am. Soc'y Nephrology, vol. 4, no. 2, pp. 142-147 (1993). The effect MA exerts on the kidneys mimics the human disease known as Fanconi Syndrome. The proposed mechanism of action of maleic acid's effect is to a) cause direct inhibition of proximal tubule Na-K-ATPase activity and b) force membrane-bound phosphorus depletion. H. Al-Bander et al., *Phosphate Loading Attenuates Renal Tubular Dysfunction Induced by Maleic Acid In the Dog*, Am. J. Physiology, vol. 248, pp. F513-F521 (1985). In dogs, this effect is seen when administered at 20 mg/kg (440 mg total dose). The human dose equivalent for this effect is predicted to be approximately 15 mg/kg (1000 mg total dose). In rats, the effect is seen when administered at 50 mg/kg (12.5 mg total dose). The human dose equivalent for this effect is predicted to be approximately 12.3 mg/kg (855 mg total dose).

MA is commonly used in non-radioactive injectable solutions (antihistamine, utertonic, chemotherapeutic) as a counter salt or to modulate pH of the injectable dose. See H. G. Boxenbaum et al., *Pharmacokinetic and Biopharmaceutic Profile of Chlordiazepoxide HCl In Healthy Subjects: Single-Dose Studies by the Intravenous, Intramuscular, and Oral Routes*, J. Pharmacokinetics & Biopharmaceuticals, vol. 5, no. 1, pp. 3-23 (1977); E. A. Peets et al., *Metabolism of Chlorpheniramine Maleate In Man*, J. Pharmacology & Experimental Therapeutics, vol. 180, pp. 364-374 (1972); R. G. Strickley et al., *Solubilizing Excipients In Oral and Injectable Formulations*, Pharmaceutical Research, vol. 21, no. 2, pp. 201-230 (2004); J. Verweij et al., "*Frequent Administration of Dabis Maleate, a Phase I Study*", Annals of Oncology, vol. 3, pp 241-242 (1992); William Sacks, *Evidence For the Metabolism of Maleic Acid In Dogs and Human Beings*, Science, vol. 127, p. 594 (1958); G. Tagliabue et al., *Antitumor Activity of 1,4-bis(2'-chloroethyl)-1,4-diazabicyclo [2.2.1]heptane dimaleate (Dabis Maleate) In M5076 and Its Subline Resistant to Cyclophosphamide M5/CTX*, Annals of Oncology, vol. 3, pp. 233-6 (1992); Maria E. L. van der Burg et al., *Phase I Study of DABIS Maleate Given Once Every 3 Weeks*, Eur. J. Cancer, vol. 27, pp. 1635-1637 (1991); J. J. M. Holthuis, *Etoposide and Teniposide: Bioanalysis, Metabolism and Clinical Pharmacokinetics*, Pharmaceutisch Weekblad Sci. Edition, vol. 10, pp. 101-116 (1998); P. Borchmann et al., *Phase I Study of BBR 2778, A New Aza-Anthracenedione, In Advanced or Refractory Non-Hodgkin's Lymphoma*, Annals of Oncology, vol. 12, pp. 661-667 (2001); J. G. Reves et al., *Midazolam Maleate Induction In Patients With Ischaemic Heart Disease: Haemodynamic Observations*, Canadian Anesthetists' Soc'y J., vol. 26, no. 5, pp. 402-409 (1979); S. M. Huang et al., *Pharmacokinetics of Chlorpheniramine After Intravenous and Oral Administration In Normal Adults*, Eur. J. Clinical Pharmacology, vol. 22, pp. 359-365 (1982). A table summary that explains under which circumstances maleic acid is injected into humans is given below (Table 2).

TABLE 2

Presence of maleic acid in human injectables

| Therapeutic/compound | Class | Status | MA Use | Total Dose |
|---|---|---|---|---|
| Methergine | Utertonic | Approved | Excipient | 0.1 mg |
| Piriton | Antihistamine | Approved | Salt form | 1.2 mg |
| BBR2778 | Chemo | Phase III | Salt form | 2.8 mg* |
| DABIS maleate | Chemo | Phase II | Salt form | 34 mg* |
| Maleic-2-$^{14}$C | Metabolism study (1958) | N/A | Direct | 11 mg |

MA is not known to stabilize radiopharmaceuticals. For example, MA was tested as a stabilizer for radiopharmaceutical $^{99m}$Tc(Sn)-DTPA with a strength of 7-9 mCi/mL. However, in the reported study, MA was "not able to prevent the decomposition of $^{99m}$Tc(Sn)-DTPA." Ralf Berger, *Radical Scavengers and the Stability of $^{99m}$Tc-Radiopharmaceuticals*, Int'l J. Applied Radiation & Isotopes, vol. 33, pp. 1341-

1344 (1982). MA has been used to prevent rancidity in fats for a period of weeks, yet MA's protective effect is diminished in the presence of water. George R. Greenbank & George E. Holm, *Antioxidants for Fats and Oils*, Indus. & Engineering Chemistry, vol. 26, no. 3, pp. 243-245 (1934).

SUMMARY OF THE INVENTION

The present invention relates to formulations, apparatuses and methods for stabilizing radiopharmaceuticals. Such radiopharmaceuticals may be positron-emitting and may comprise, for example, [F-18]fluoride or [C-11]carbon. One radiopharmaceutical may be [F-18]FDG. Others may include [F-18]FMAU, [F-18]FMISO, [F-18]FHBG, [F-18]AV-45, [F-18]AV-19, [F-18]AV-1, [F-18]Flutemetamol, [F-18]Flurpiridaz, [F-18]K5, [F-18]HX4, [F-18]W372, [F-18]VM4-037, [F-18]CP18, [F-18]ML-10, [F-18]T808, [F-18]T807 and 2-[F-18]fluoromethyl-L-phenylalanine. It is envisioned that virtually any radiopharmaceutical may be used and stabilized with the present formulation. Such may have radiolabels selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$. The formulations, apparatuses and methods preferably comprise a gas of about 10 vol. % to about 100 vol. % oxygen as a stabilizer in the presence of an excipient such as maleic acid. Oxygen may refer to substantially pure $O_2$ or "air", which may comprise smaller amounts of nitrogen, carbon dioxide, argon, etc.

In one embodiment, the present invention is a formula for stabilizing a radiopharmaceutical. The formula comprises a solution comprising a radiopharmaceutical, a stabilizer and water. The stabilizer may be an oxidant such as oxygen. The stabilizer may also be an excipient such as maleic acid. A gas may include the oxidant in an amount of about 21 vol. %. The formula may also comprise inorganics such as phosphates, sodium chloride, sodium bicarbonate, HCl, NaOH, etc. The formula may further comprise an inorganic salt. Such salts include but are not limited to phosphates such as $NaH_2PO_4$, $Na_2HPO_4$ and $Na_3PO_4$. The formula may also comprise an alcohol such as ethanol.

In another embodiment, the present invention is an apparatus for stabilizing a radiopharmaceutical. The apparatus comprises a container having a formula comprising a radiopharmaceutical, the stabilizer and water. The stabilizer preferably comprises maleic acid. The container may be sealable and, when sealed, be substantially impermeable to oxygen.

In another embodiment, the present invention is a method of making a formula for stabilizing a radiopharmaceutical. The method comprises providing a radiopharmaceutical, providing a stabilizer and providing water. Preferably, the stabilizer is maleic acid. An alcohol such as ethanol and a salt such as a phosphate may also be provided.

We have shown that 8 vol. % EtOH:92 vol. % sodium phosphate (21 mM, pH=4.0-7.0) containing 0.01% (g/ml) maleic acid is very efficient at stabilizing [F-18]FLT.

DETAILED DESCRIPTION OF EMBODIMENTS

Figure 1:
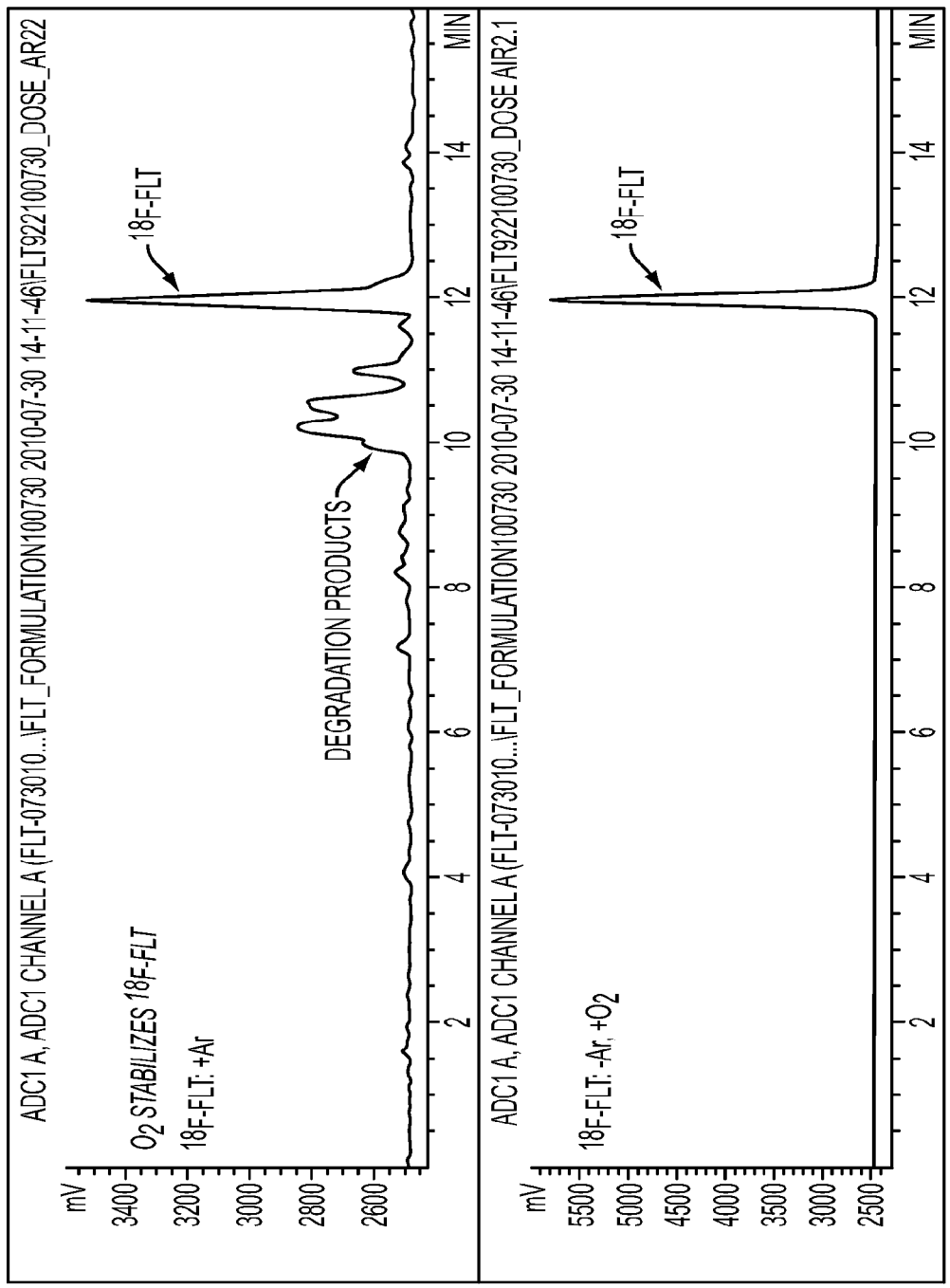
FIG. 1 is a graph showing how [F-18]FLT decomposes in the presence of argon without oxygen (upper trace) and how [F-18]FLT is stabilized in the presence of oxygen (lower trace).
Figure 2:
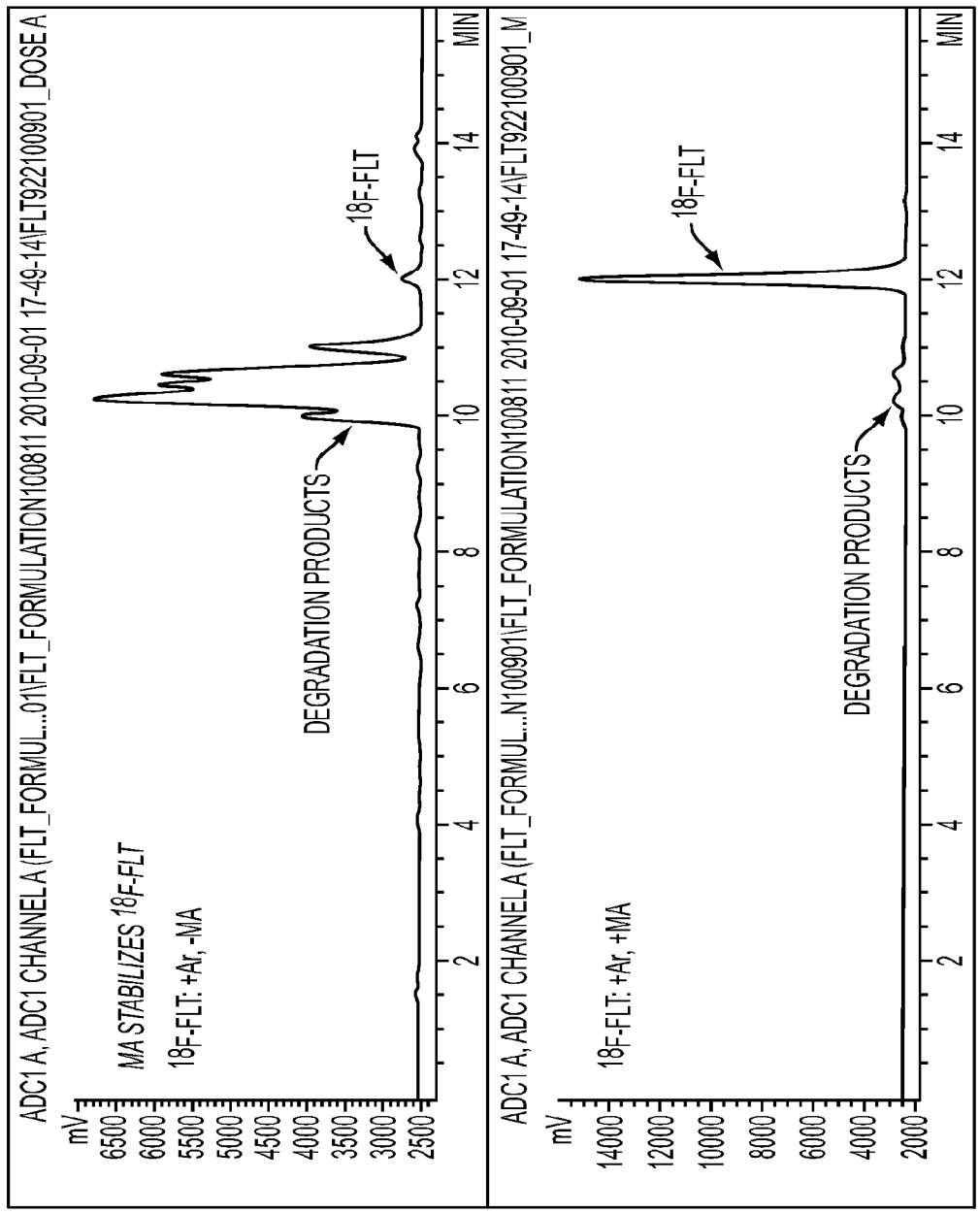
FIG. 2 is a graph showing how [F-18]FLT decomposes in the presence of argon without maleic acid and how [F-18]FLT is stabilized in the presence of maleic acid in argon.
Figure 3:
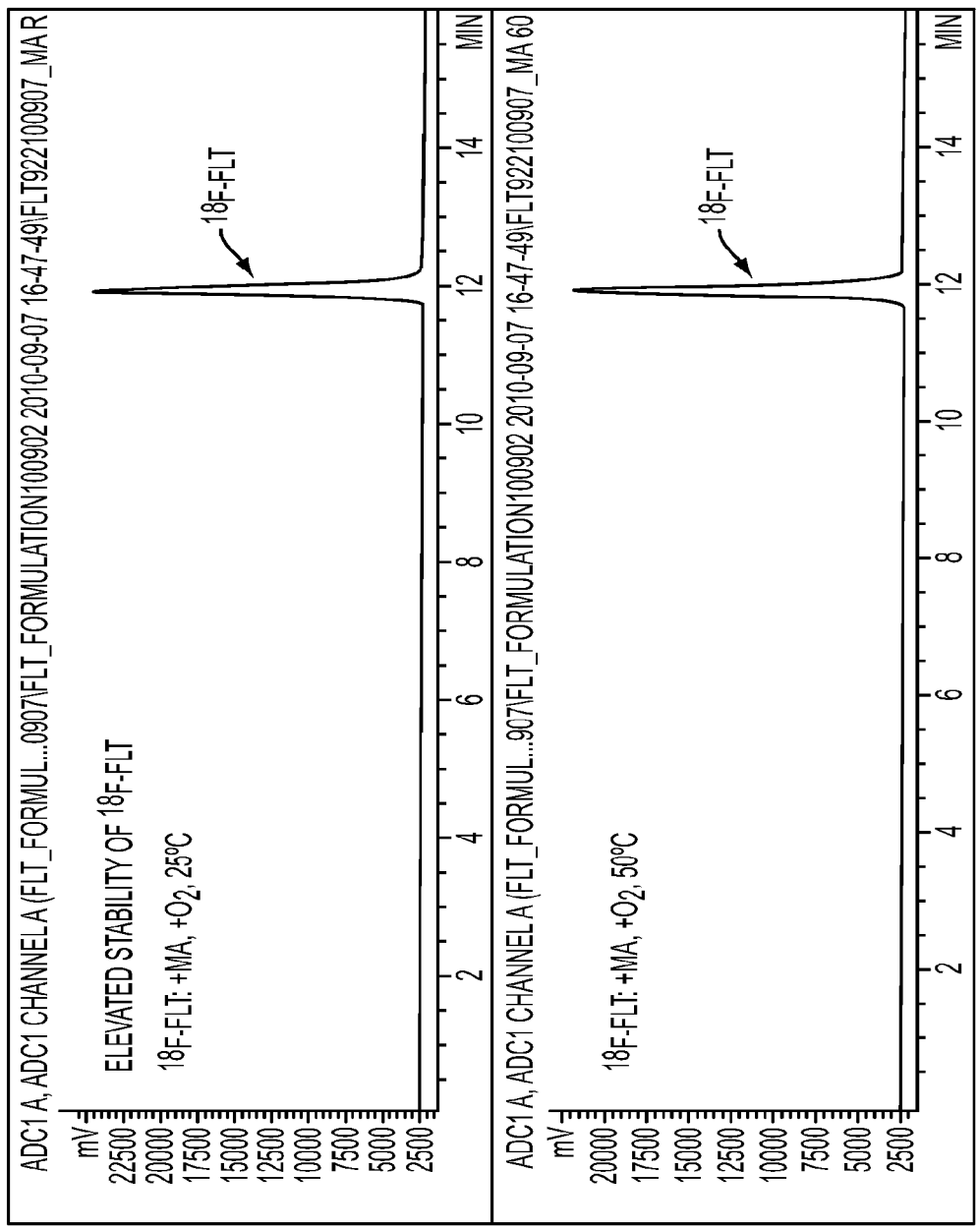
FIG. 3 is a graph showing how [F-18]FLT containing maleic acid and air (oxygen: 20.95 vol. %) are equally stable at 50° C. for a period of 2 hours.
Figure 4:
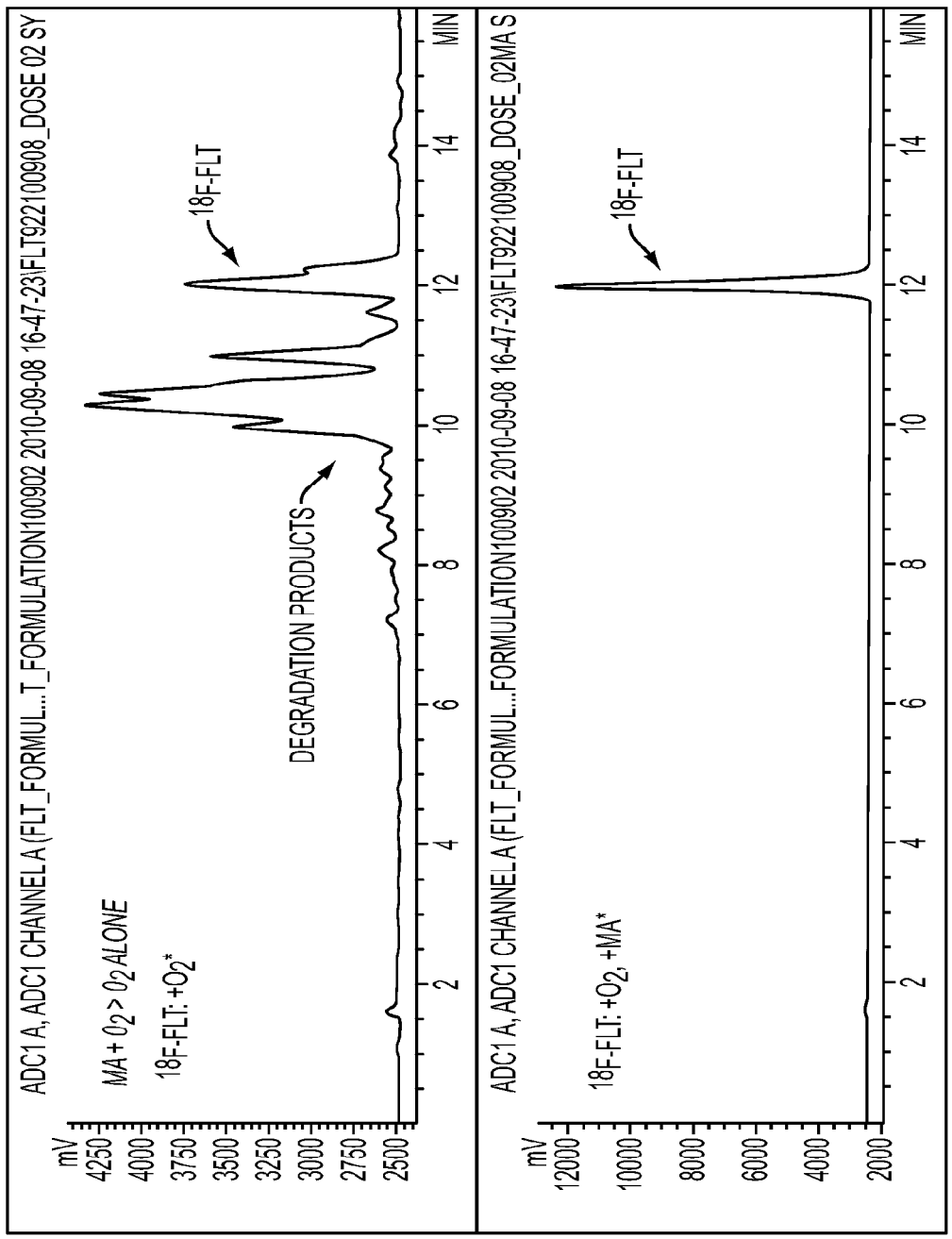
FIG. 4 is a graph showing how [F-18]FLT decomposes in the presence of oxygen once the oxygen is consumed and how [F-18]FLT is further stabilized in the presence of oxygen and maleic acid.

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Unless otherwise specified, the percentages of various constituents in liquid phases discussed below (including gases dissolved in a liquid phase) are mass per mass percentages (as mass of constituent over total mass), or volume per volume percentages (as volume of constituent over total volume), as a percentage of a given phase. For example, a percentage of ethanol being around 8 vol. % is given as a percentage of the total liquid phase. Similarly, a percentage of oxygen being around 20.95 vol. % is given as a percentage of the total gas phase (e.g., headspace). The only exception is that the percentage of maleic acid is given as a mass per liquid volume percentage, as grams of maleic acid over total liquid volume in milliliters. For example, 0.1 mg/ml of maleic acid equals 0.0001 g/ml. To then get the percentage of maleic acid, the concentration in grams per milliliter is multiplied by 100%, arriving at a percentage of 0.01% maleic acid (which corresponds to the FDA's maximum potency for maleic acid).

As used below, the terms "sparge", "sparged", "sparging", and other similar variations refer both to sparging by filling a headspace with a sparging gas to remove an unwanted gas, and to sparging by bubbling the sparging gas through a liquid to remove the unwanted gas.

In the present invention, radiopharmaceutical formulations should contain a gas having between about 10 vol. % and about 100 vol. % oxygen in the bulk vial, in solution and also in the vial headspace. In some embodiments, the formulation comprises a gas of about 20.95 vol. % oxygen. The radiopharmaceutical formulation may also contain a stabilizer such as maleic acid, with a maximum amount of maleic acid being 0.5% (as grams of maleic acid per total milliliter of liquid). This novel stabilizing effect has been demonstrated to provide a unique stabilizing effect which efficiently guards against many types of degradation including radiolysis. One way in which the present invention distinguishes itself from existing formulations is through the presence of oxygen in the final formulation of PET radiopharmaceuticals to prevent radiolysis. Contrary to the cited literature, in the formulation of the present invention, oxygen prevents radiolysis, rather than promoting radiolysis. Secondly, the use of maleic acid to stabilize radiopharmaceuticals is not known in the art. Lastly, the synergistic combination of oxygen and maleic acid to stabilize radiopharmaceuticals is not known in the art.

In the formulation of the present invention, the synergistic combination of oxygen and maleic acid was discovered to possess a unique ability to stabilize [F-18]FLT in dosing solutions with high strength for a period of 4 to 10 hours. Preferably, the strength of the dosing solution is at least 10 mCi/ml. More preferably, the strength of the dosing solution is at least 30 mCi/ml. Even more preferably, the strength of the dosing solution is at least 60 mCi/ml to over 120 mCi/ml. In some instances, the formulation was stable for about 18 hours. The formulations were stored at temperatures of about 0° C. to about 50° C. Formulations of [F-18]FLT which are devoid of oxygen rapidly decomposed within a 2 to 3 hour timeframe. Stabilized samples of [F-18]FLT containing $O_2$ had higher amounts of hydrogen peroxide present in solution than radiolyzed samples that contained no $O_2$. Therefore, samples of [F-18]FLT spiked with $O_2$, and ultimately hydrogen peroxide, did not contain radiolyzed products up to 197 mCi/mL. This suggests that $O_2$ spiked solutions prevented radiolysis through a protective mechanism while simultaneously generating hydrogen peroxide. Therefore, the presence $O_2$ is linked to the formation of hydrogen peroxide. When samples were devoid of $O_2$ but contained maleic acid as the stabilizer, very little hydrogen peroxide was formed yet radiolytic decomposition was also greatly slowed. The presence of oxidants or electron deficient compounds, such as maleic acid, appear to stabilize [F-18]FLT and other radiopharmaceuticals from radiolytic degradation. Therefore, without being bound by theory, it appears that the presence of oxygen and maleic acid in this formulation is critical and advantageous for the preparation of [F-18]FLT in high strength while preserving radiochemical purity. The use of oxygen and maleic acid as stabilizers in this formulation is surprisingly effective, yet easy to handle in its sterile form and is fully biocompatible for human injection.

The invention will now be illustrated by the following examples.

EXAMPLES

[F-18]FLT was prepared on an explora GN synthesis module using the Boc-Boc-Nos FLT precursor. (See, e.g., U.S. Pat. No. 7,160,537, which is incorporated by reference). It will be understood that other methods of formulating [F-18]FLT may be used in conjunction with the present invention. The [F-18]FLT was purified by reverse phase C18 semi-preparative HPLC using 8 vol. % EtOH:92 vol. % 21 mM sodium phosphate. When MA was used in the formulation, it was introduced into the radiopharmaceutical by either spiking with a small volume of a 1 g/100 mL solution or alternatively introduced into the mobile phase. [F-18]FLT was purified by reverse phase C18 semi-preparative HPLC using 8 vol. % EtOH: 92 vol. % 21 mM sodium phosphate containing 0.01% (g/ml) maleic acid. The collected HPLC fraction was passed over an $Al_2O_3$ cartridge followed by sterile filtration into a pyrogen-free sterile vial. The radiochemical purity of [F-18]FLT was measured by radio-analytical HPLC equipped with a gamma detector. It will be understood that other methods of purifying [F-18]FLT may be used in conjunction with the present invention. The analysis was performed using a MeCN:water gradient on a C18 column with a 1 mL/min flow rate. The percent stability is defined as the ratio between the area of parent [F-18]FLT versus the remaining [F-18]-labeled by-products. A headspace of oxygen refers to a gaseous mixture of about 20.95 vol. % oxygen. [F-18] HX4, [F-18]W372 and [F-18]BMS757158-02 were prepared according to published procedures. Other excipients that were used to stabilize [F-18]FLT include beta-cyclodextrin, methylene blue, alpha-cyclodextrin, gentisic acid, cyclohexane dione diamine, ascorbic acid, thioglycerol, glutathione, tartaric acid, niacinamide, ascorbic acid, $FeCl_3$, $H_2O_2$, glutamic acid, triamine pentaacid, methylene diphosphonic acid, beta-hydroxypropyl cyclodextrin, xanthine, aspartic acid, chlorobutanol, calcium chloride, mannitol, creatanine, calcium gluconate, dimethyl acetamide, diazatriazoic acid, sodium succinate, boric acid and sodium carbonate. Hydrogen peroxide concentration (ppm) was determined using peroxide test strips.

Example 1

A solution of [F-18]FLT (126.8 mCi/mL at EOS), formulated in 8 vol. % EtOH:92 vol. % phosphate, was kept either with a headspace of 20.95 vol. % oxygen (dose vial) or without a headspace of oxygen (syringe). As shown in Table 3, after 3.5 hrs, the solution of [F-18]FLT without the headspace of oxygen decomposed to 65% radiochemical purity. The sample with the headspace of oxygen remained radiochemically intact. This data supports the finding that oxygen provides a stabilizing effect on [F-18]FLT in aqueous ethanol.

TABLE 3

Shows percent stability after 3.5 hours for a syringe without oxygen and vial with oxygen-filled headspace.

| FLT batch | mCi/mL at EOS | formulation | analysis method | % stability 3.5 hr |
|---|---|---|---|---|
| 100728-syringe-NO HEADSPACE | 126.8 | 8 vol. % EtOH: 92 vol. % phosphate | HPLC | 65 |
| 100728-dose vial-HEADSPACE | 126.8 | 8 vol. % EtOH: 92 vol. % phosphate | HPLC | 99.9 |

Example 2

A solution of [F-18]FLT (129.5 mCi/mL at EOS), formulated in 8 vol. % EtOH:92 vol. % phosphate, was drawn into a syringe with either a headspace of oxygen (20.95 vol. %) or without a headspace of oxygen. Initially, both samples were stable. After 2.6 hrs, however, the solution of [F-18]FLT without the headspace of oxygen decomposed to 66.7% radiochemical purity. The sample continued to further degrade to 32.7% radiochemical purity after 3.8 hrs. The sample with the headspace of oxygen remained radiochemically intact. As a control, a dose vial with a headspace of oxygen also remained radiochemically intact. This data supports the finding that oxygen provides a stabilizing effect on [F-18]FLT in aqueous ethanol in syringes.

TABLE 4

Shows percent stability at various time intervals for a syringe without headspace and, therefore, no oxygen, a syringe with headspace and, therefore, oxygen and a dose vial with oxygen.

| FLT batch | mCi/mL at EOS | formulation | analysis method | % stability 0.5 hr | % stability 1.6 hr | % stability 2.6 hr | % stability 3.8 hr |
|---|---|---|---|---|---|---|---|
| 100729-syringe NO HEADSPACE | 129.5 | 8 vol. % EtOH:92 vol. % phosphate | HPLC | 100 | 100 | 66.7 | 32.7 |
| 100729-syringe-HEADSPACE | 129.5 | 8 vol. % EtOH:92 vol. % phosphate | HPLC | 100 | 100 | 99.5 | 99.6 |
| 100729-dose vial-HEADSPACE | 129.5 | 8 vol. % EtOH:92 vol. % phosphate | HPLC | 100 | 99.4 | 99.8 | 99.2 |

Example 3

A solution of [F-18]FLT (63.2 mCi/mL at EOS), formulated in 8 vol. % EtOH:92 vol. % phosphate, was drawn into a syringe with headspace of oxygen (20.95 vol. %). A second sample was transferred into a second vial purged with a gas having 20.95 vol. % oxygen. The dose vial was sparged with Ar to remove oxygen. After 1.5 hrs, the dose vial containing [F-18]FLT which was sparged with Ar, decomposed to 62.5% radiochemical purity. This sample continued to further degrade to 38.57% radiochemical purity after 4.0 hrs. The samples with the headspace of oxygen (both the syringe and sample vial) remained radiochemically intact up to 4 hrs. This data supports the finding that oxygen provides a stabilizing effect on [F-18]FLT in aqueous ethanol in bulk vials with oxygen dissolved in solution as well as being present in the vial headspace.

TABLE 5

Shows percent stability at various time intervals for a syringe with headspace, an Argon sparged dose vial and an $O_2$-purged dose vial.

| FLT batch | mCi/mL at EOS | formulation | analysis method | % stability 0.5 hr | % stability 1.5 hr | % stability 4 hr |
|---|---|---|---|---|---|---|
| 100730-syringe-HEADSPACE | 63.2 | 8 vol. % EtOH:92 vol. % phosphate | HPLC | 100 | 100 | 100 |
| 100730-Ar sparged dose vial | 63.2 | 8 vol. % EtOH:92 vol. % phosphate | HPLC | — | 62.5 | 38.5 |
| 100730-$O_2$ purged dose vial | 63.2 | 8 vol. % EtOH:92 vol. % phosphate | HPLC | — | 100 | 100 |

This data supports the finding that oxygen provides a stabilizing effect on [F-18]FLT in aqueous ethanol.

A solution of [F-18]FLT (28.5 mCi/mL after reformulation or 16.2 mCi/mL after reformulation), formulated in either 10 vol. % EtOH:water or 8 vol. % EtOH:92 vol. % phosphate, in vials with either a headspace of argon or air (oxygen: 20.95 vol. %). After 1 hrs, the dose vial containing [F-18]HX4 in 10 vol. % EtOH:water, which was sparged with Ar, decomposed to 0.28% radiochemical purity (Table 6). This sample continued to further degrade to 0% radiochemical purity after 4.0 hrs. The sample with the headspace of oxygen remained radiochemically intact up to 4 hrs. The [F-18]HX4 in 8 vol. % EtOH:92 vol. % phosphate with a headspace of argon decomposed to 85.6% radiochemical purity after 3 hrs. In the presence of air, the radiochemical purity was 94.06%. This data supports the finding that oxygen stabilizes [F-18]HX4 against radiolytic decomposition.

TABLE 6

Solutions of [F-18]HX4 aged in either the presence of air (20.95 vol. % oxygen) or argon. Samples aged in the presence of air (20.95 vol. % oxygen) were more stable than those samples aged under argon.

| Sample | mCi/mL | formulation | Additive | % stability 1 hr | % stability 3 hr | % stability 4 hr |
|---|---|---|---|---|---|---|
| HX4-922-100805-AIR | 28.5 | 10 vol. % EtOH:water | Air ($O_2$) | 98.33 | — | 99.01 |
| HX4-922-100805-AR purged | 28.5 | 10 vol. % EtOH:water | Argon | 0.28 | — | 0 |

TABLE 6-continued

Solutions of [F-18]HX4 aged in either the presence of air (20.95 vol. % oxygen) or argon. Samples aged in the presence of air (20.95 vol. % oxygen) were more stable than those samples aged under argon.

| Sample | mCi/mL | formulation | Additive | % stability 1 hr | % stability 3 hr | % stability 4 hr |
|---|---|---|---|---|---|---|
| HX4-922-100909 | 16.2 | 8 vol. % EtOH:phosphate | Air ($O_2$) | — | 94.06 | — |
| HX4-922-100909 | 16.2 | 8 vol. % EtOH:phosphate | Argon | — | 85.6 | — |

Example 5

An aerated sample of [F-18]BMS 747158-02 (12 mCi/mL), formulated in 10 vol. % EtOH:water was set aside for aging. The remaining solution was sparged with Ar to remove oxygen. After 2.25 hrs, the dose vial containing [F-18]BMS 747158-02 sparged with Ar, decomposed to 12% radiochemical purity. The aerated sample with had a radiochemical purity of 91% after 2.25 hrs. This data supports the finding that oxygen stabilizes [F-18]BMS 747158-02 against radiolytic decomposition.

TABLE 7

Solutions of [F-18]BMS 757158-02 were more stable in air (oxygen) than in argon.

| BMS 747158-02 | mCi/mL at EOS | formulation | additive | % stability 2.25 hr |
|---|---|---|---|---|
| BMS-922-100824 | 12 | 10 vol. % EtOH:water | Air/O$_2$ (before sparge) | 91 |
| BMS-922-100824 | 12 | 10 vol. % EtOH:water | Argon (reformulated after sparge) | 12 |

Example 6

A aerated sample of [F-18]W372 (19.2 mCi/mL), formulated in 10 vol. % EtOH:water was set aside for aging. The remaining solution was sparged with Ar to remove oxygen. After 1.5 hrs, the dose vial containing [F-18]W372 sparged with Ar, decomposed to 94.6% radiochemical purity. The sample with the headspace of oxygen had a radiochemical purity of 97.6% after 1.5 hrs. This data supports the finding that oxygen stabilizes [F-18]W372 against radiolytic decomposition.

TABLE 8

Solutions of [F-18]W372 were more stable in air (oxygen) than in argon.

| Sample | mCi/mL | formulation | additive | % stability 1.5 hr |
|---|---|---|---|---|
| W372-922-100907 | 19.2 | 10 vol. % EtOH:water | Argon | 94.6 |
| W372-922-100907 | 19.2 | 10 vol. % EtOH:water | O$_2$ | 97.6 |

Example 7

A solution of [F-18]FLT (103 mCi/mL), formulated in 8 vol. % EtOH:phosphate, was sparged with argon to remove oxygen in the sample. An aliquot was removed and spiked with degassed maleic acid. Both samples were aged for 4 hrs. After 4 hrs, the sample without maleic acid had a radiochemical purity of 1.5%. The sample containing maleic acid had a radiochemical purity of 88.7%. This data supports the stabilizing effect of maleic acid on [F-18]FLT. Hydrogen peroxide was measured using test strips. The FLT sample (126.3 mCi/mL) containing a headspace of argon contained no detectable hydrogen peroxide (i.e. 0 ppm). The FLT sample (126.3 mCi/mL) containing maleic acid contained no detectable hydrogen peroxide (i.e. 0 ppm).

TABLE 9

[F-18]FLT aged in argon containing maleic acid was more stable than a sample of [F-18]FLT aged in argon without maleic acid.

| Sample | mCi/mL | formulation | additive | % stability 4.0 hr |
|---|---|---|---|---|
| FLT-922-100901 | 126.3 | 8 vol. % EtOH:phosphate | Ar | 1.5 |
| FLT-922-100901 | 126.3 | 8 vol. % EtOH:phosphate | maleic acid (0.1 mg/mL) and Ar | 88.77 |

Example 8

A sample of [F-18]FLT (118 mCi/mL), formulated in aerated 8 vol. % EtOH:phosphate, was removed for aging. The headspace in the remaining sample was sparged with argon to remove oxygen. After 3.25 hrs, the sample with maleic acid under argon had a radiochemical purity of 37.9%. The sample containing maleic acid in oxygen had a radiochemical purity of 99.8%. This data supports the increased stabilizing effect of maleic acid on [F-18]FLT in air over argon.

TABLE 10

Samples of [F-18]FLT containing maleic acid showed differing stability when aged in the presence of air versus argon. The sample aged in air was more stable than the sample stored under argon.

| Sample | mCi/mL | formulation | additive | % stability 3.25 hr |
|---|---|---|---|---|
| FLT-922-100903 | 118.7 | 8 vol. % EtOH:phosphate | maleic acid + Air headspace | 99.8 |
| FLT-922-100903 | 118.7 | 8 vol. % EtOH:phosphate | maleic acid + Ar headspace | 37.9 |

Example 9

Solutions of [F-18]FLT (82 mCi/mL), formulated in aerated 8 vol. % EtOH:phosphate, containing 0.01% (g/ml) maleic acid were aged for 2 hours at either room temperature or at 50° C. After 2 hrs, both samples had a radiochemical purity of 100%. This data supports the finding that maleic acid does not cross-react with [F-18]FLT at either elevated or room temperature.

TABLE 11

Samples of [F-18]FLT containing maleic acid and air were equally stable at 50° C. for a period of 2 hours.

| Sample | mCi/mL | formulation | additive | % stability 2 hr |
|---|---|---|---|---|
| FLT-922-100907 | 82 | 8 vol. % EtOH:phosphate | maleic acid + Air headspace (rt) | 100 |
| FLT-922-100907 | 82 | 8 vol. % EtOH:phosphate | maleic acid + Air headspace (50 C.) | 100 |

Example 10

An aerated sample of [F-18]FLT (197 mCi/mL) formulated in 8 vol. % EtOH:92 vol. % phosphate was either spiked or not spiked with maleic acid (0.1 mg/mL). The samples were aged for 3.5 hrs. After this time, the sample not containing maleic acid had a radiochemical purity of 82.6%. The spiked sample had a radiochemical purity of 99.2%.

In a separate experiment, [F-18]FLT (127 mCi/mL) formulated in 8 vol. % EtOH:92 vol. % phosphate was either spiked or not spiked with maleic acid (0.1 mg/mL) and additional aliquots were drawn into syringes without a headspace of air. The samples were aged for 5.5 hours. While the vial samples remained radiochemically intact (98% or greater) with or without maleic acid, the syringe samples varied remarkably. The sample aged in the syringe without maleic acid had a radiochemical purity of 19.68%. The syringe sample containing maleic acid had a radiochemical purity of 97.13%. The experiment shows the synergistic stabilization effect of maleic acid and oxygen in stabilizing [F-18]FLT. Hydrogen peroxide was measured using test strips. The FLT sample (127 mCi/mL) containing a headspace of oxygen contained hydrogen peroxide with a concentration of 5 ppm. The FLT sample (127 mCi/mL) containing a headspace of oxygen and maleic acid contained hydrogen peroxide with a concentration of 0.5-2.0 ppm.

TABLE 12

Bulk vials of [F-18]FLT containing a headspace of air, dissolved air and maleic acid are more stable than [F-18]FLT containing only a headspace of air and dissolved air. This was further confirmed in aged syringe samples in which the maleic acid spiked sample was more stable than the sample without maleic acid.

| Sample | mCi/mL | formulation | additive | % stability 3.5 hr | % stability 5.5 hr |
|---|---|---|---|---|---|
| FLT-922-100909 | 197.1 | 8 vol. % EtOH:phosphate | maleic acid + O2 | 99.2 | — |
| FLT-922-100909 | 197.1 | 8 vol. % EtOH:phosphate | FLT dose vial (air/O2 only) | 82.6 | — |
| FLT-922-100908 | 127 | 8 vol. % EtOH:phosphate | maleic acid + Air headspace (rt) | — | 99.48 |
| FLT-922-100908 | 127 | 8 vol. % EtOH:phosphate | Air headspace | — | 98 |
| FLT-922-100908 (syringe sample) | 127 | 8 vol. % EtOH:phosphate | maleic acid + O2 (no headspace) | — | 97.13 |
| FLT-922-100908 (syringe sample) | 127 | 8 vol. % EtOH:phosphate | O2 (no headspace) | — | 19.68 |

Example 11

A sample of [F-18]W372 (19.2 mCi/mL) formulated in aerated 10 vol. % EtOH:water containing 0.01% (g/ml) maleic acid was set aside for aging. The remaining sample was purged with argon to remove oxygen. The samples were aged for 1.5 hours. The sample aged under argon had a radiochemical purity of 90.1%. The sample stored in the presence of air had a radiochemical purity of 94.9%. This data supports the increased stability of [F-18]W372 in the presence of maleic acid and oxygen.

TABLE 13

A sample of [F-18]W372 aged in maleic acid and air (oxygen: 20.95 vol. %) was more stable than a sample aged with maleic acid in argon.

| Sample | mCi/mL | formulation | additive | % stability 1.5 hr |
|---|---|---|---|---|
| W372-922-100907 | 19.2 | 10 vol. % EtOH:water | maleic acid + O2 | 94.9 |
| W372-922-100907 | 19.2 | 10 vol. % EtOH:water | maleic acid + Argon | 90.1 |

Example 12

A sample of [F-18]HX4 (16.2 mCi/mL) formulated in aerated 10 vol. % EtOH:water containing 0.01% (g/ml) maleic acid was set aside for aging. The remaining sample was purged with argon to remove oxygen. The samples were aged for 3 hours. The sample under argon had a radiochemical purity of 8.66%. The sample stored in the presence of air had a radiochemical purity of 98.9%. This data supports the increased stability of [F-18]HX4 in the presence of maleic acid and oxygen.

TABLE 14

[F-18]HX4 stored in the presence of maleic acid and oxygen is more stable than when stored in the presence of maleic acid and argon.

| Sample | mCi/mL | formulation | additive | % stability 3 hr |
|---|---|---|---|---|
| HX4-922-100909 | 16.2 | 8 vol. % EtOH:phosphate | maleic acid + O2 | 98.9 |
| HX4-922-100909 | 16.2 | 8 vol. % EtOH:phosphate | maleic acid + Argon | 8.66 |

Example 13

Dose vials of [F-18]FLT were formulated in 8 vol. % EtOH:92 vol. % phosphate and degassed via argon sparging. Aliquots from the dose vial (typically 1 mL) were withdrawn and placed into argon sparged vials containing various excipients (typically 50 mg). The samples were aged (1 to 5 hours) and the radiochemical purity of [F-18]FLT was determined. Several excipients were found to stabilize [F-18]FLT against radiolysis in the presence of argon. Other excipients destabilized or had no effect on the stabilization of [F-18]FLT in the presence of argon in aqueous ethanol. The protective factor (PF) was determined by dividing the percent radiochemical stability of the excipient-doped dose by the percent radiochemical stability of the argon-sparged dose. The results are shown in Table 15. One excipient that was found to be highly stabilizing in the absence of oxygen, and in the presence of argon, was maleic acid. Ascorbic acid, a known radiopharmaceutical stabilizer and anti-oxidant, was not as effective in stabilizing [F-18]FLT against radiolysis at 50 mg/mL as compared to oxygen.

TABLE 15

A summary of excipients that were screened for their
protective effect in stabilizing [F-18]FLT.

| Stabilizing (PF > 1.1) | No Effect (PF 1.1 to 1.0) | Destabilizing (PF < 1.0) |
|---|---|---|
| chlorobutanol | glutamic acid | Ar |
| creatanine | Ascorbic acid | $N_2$ |
| $O_2$ | alpha-cyclodextrin | Ar + $FeSO_4$ + $H_2O_2$ |
| dimethyl acetamide | Ar + $H_2O_2$ | methylene diphosphonic acid |
| diazatriazoic acid | beta-cyclodextrin | aspartic acid |
| Maleic acid | methylene blue | beta-hydroxypropyl cyclodextrin |
| $O_2$ + maleic acid | triamine pentaacid | Xanthine |
| Glutathione | Ar + $FeSO_4$ | Calcium gluconate |
| $H_2O_2$ | tartaric acid | mannitol |
| niacinamide | | Calcium Chloride |
| cyclohexane dione diamine | | Sodium Succinate |
| triethanolamine | | boric acid |
| $FeCl_3$ | | sodium carbonate |
| thioglycerol | | Boric acid |
| Gentisic acid | | Sodium carbonate |

Example 14

Figure 5:
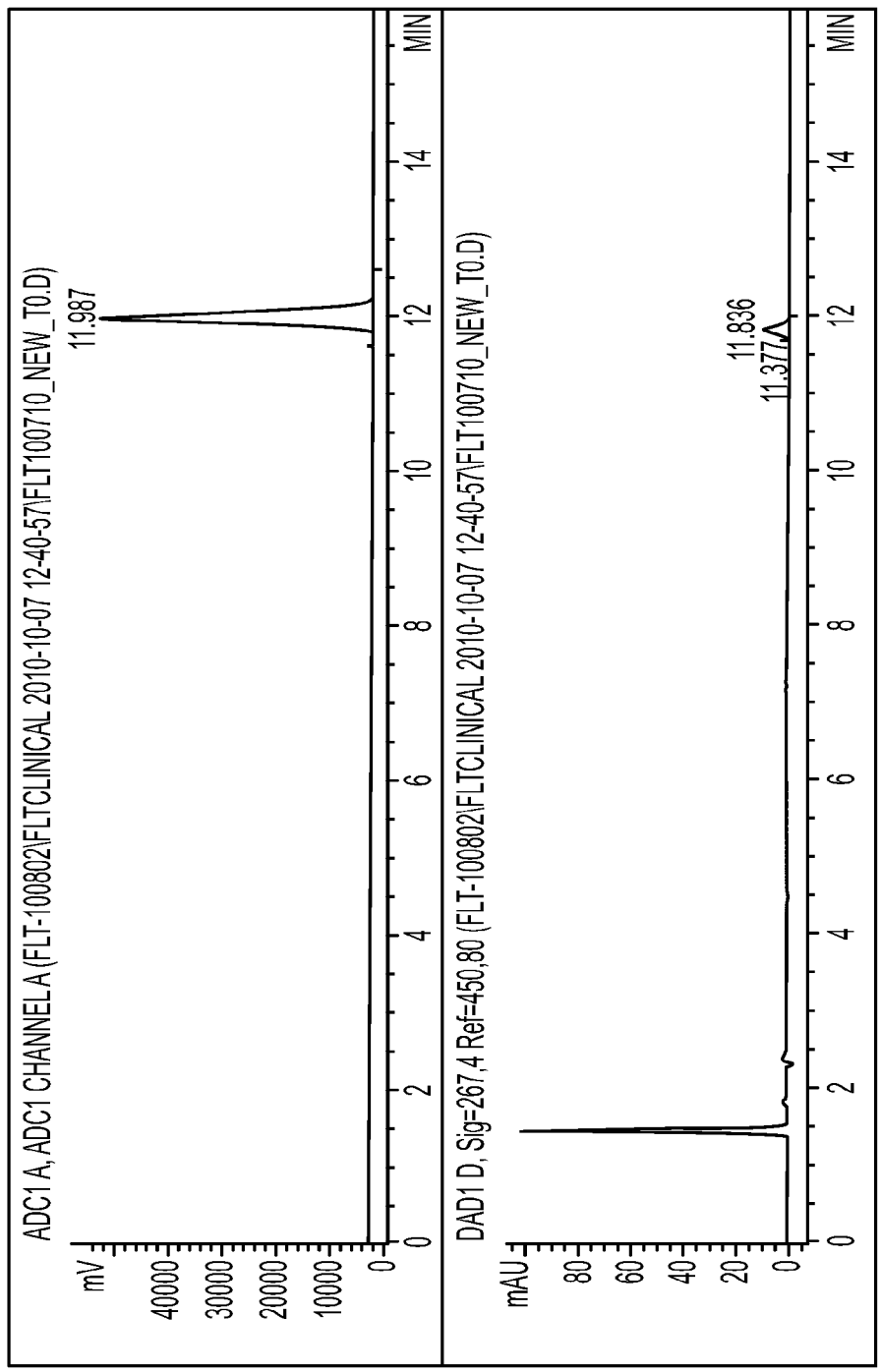
FIG. 5 is a graph showing how [F-18]FLT is formulated in EtOH:phosphate containing 0.01% (g/ml) maleic acid at EOS. The top trace is the radioactivity trace; the bottom trace is the UV trace.
Figure 6:
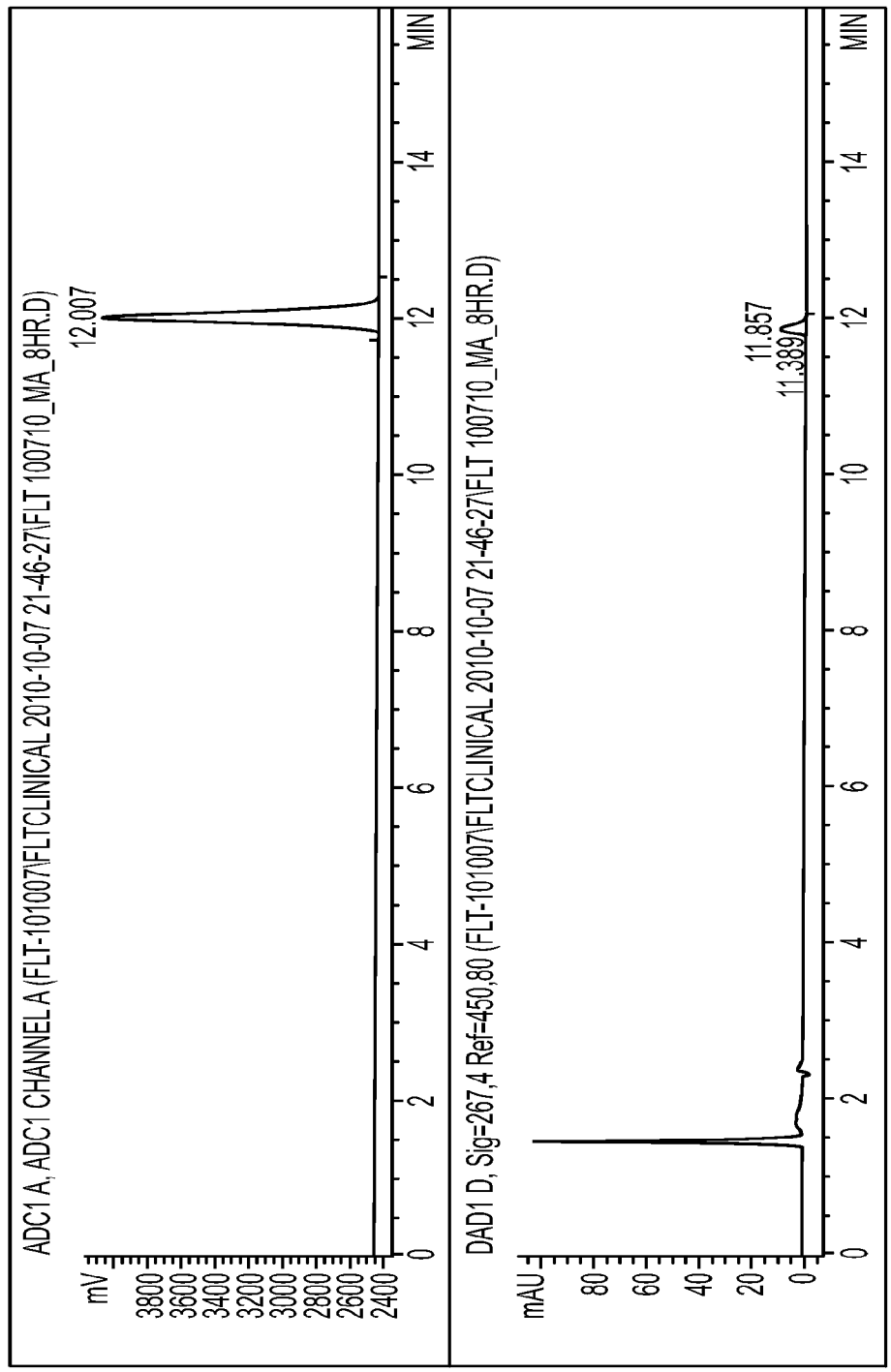
FIG. 6 is a graph showing how [F-18]FLT is formulated in EtOH:phosphate containing 0.01% (g/ml) maleic acid at 8 hrs post EOS. The top trace is the radioactivity trace, the bottom trace is the UV trace. There is no change in the chemical or radiochemical signal after aging.

A solution of [F-18]FLT (50 mCi/mL at EOS), formulated in aerated 8 vol. % EtOH:92 vol. % phosphate containing 0.01% (g/ml) maleic acid (FIG. 5), was aged in a sterile vial in air for a period of 8 hrs. After 8 hrs, the chemical and radiochemical analysis indicated that [F-18]FLT did not undergo any decomposition during this aging period (FIG. 6).

Example 15

It was further confirmed that the presence of air in a container headspace provides protection against radiolysis by a storing FLT in containers with air in the vial headspace or following sparging of a vial with Argon to displace residual air and measuring RCP over time.

| Container | RCP % 1.5 hrs post dispensing | RCP % 4 hrs post dispensing |
|---|---|---|
| Air-purged vial | 100 | 100 |
| Argon purged vial | 62.5 | 38.5 |

This showed that air does have a stabilizing effect on FLT under these experimental conditions.

In order to further assess the stability of FLT in air-filled sterile vials, vials were sourced from a company called Greer in the United States of America.

A summary of the stability data for radiochemical purity ("RCP") in two trial batches using the Greer vial is provided in the table below.

| FLT Batch Number | RCP % t0 | RCP % 5 hrs post dispensing | RCP % 10 hrs post dispensing |
|---|---|---|---|
| 54-T-280710-1 | 100 | 96.5 | — |
| 54-T-300710-1 | 100 | 100 | 100 |

Although some degradation was reported this did not exceed the specified limit of <5% radiochemical impurities.

In order to further assess the effect of oxygen on RCP, vials from Greer and another company (Adelphi) were used to test the effect of varying percentages of oxygen in the headspace. A summary of this stability data is shown below.

| ITN or Lot | Supplier | O2 vol. % In Headspace | N2 vol. % In Headspace | FLT RCP results |
|---|---|---|---|---|
| 763 | Adelphi | 10.74 | 87.24 | Good |
| 763 | Adelphi | 10.36 | 87.62 | Good |
| 763 | Adelphi | 10.17 | 87.79 | Good |
| 763 | Adelphi | 10.24 | 87.74 | Good |
| 763 | Adelphi | 10.67 | 87.30 | Good |
| 1030 | Adelphi | 5.15 | 92.83 | Bad |
| 1030 | Adelphi | 5.17 | 92.80 | Bad |
| 1030 | Adelphi | 5.21 | 92.76 | Bad |
| 1030 | Adelphi | 5.12 | 92.83 | Bad |
| 1030 | Adelphi | 5.04 | 92.93 | Bad |
| 155500 | Greer | 19.57 | 78.25 | Good |
| 155500 | Greer | 19.60 | 78.21 | Good |
| 155500 | Greer | 19.57 | 78.24 | Good |
| 155500 | Greer | 19.66 | 78.12 | Good |
| 155500 | Greer | 19.53 | 78.28 | Good |
| 54-T-300108-1 Vial 9 | Adelphi | 11.00 | 86.99 | Good |
| 54-T-310108-1 Vial 9 | Adelphi | 11.22 | 86.77 | Good |
| 54-T-100609-1 Vial 9 | Adelphi | 13.56 | 84.42 | Good |
| 54-T-110609-1 Vial 9 | Adelphi | 13.15 | 84.85 | Good |
| 54-T-170709-1 Vial 9 | Adelphi | 14.65 | 83.33 | Good |

As can be seen above, the FLT stability is improved when oxygen is present in the finished product vial headspace in a percentage of above around 10 vol. %.

Example 16

[F-18]VM4-037 and [F-18]K5 were found to be susceptible to radiolytical decomposition when stored under an atmosphere of He. When oxygen was introduced into the sample vials, [F-18]VM4-037 and [F-18]K5 were found to not undergo radiolysis.

Example 17

The stabilizing effect of ascorbic acid was examined with and without a headspace of air. In entries 1 through 8, ascorbic acid does indeed stabilize [F-18]FLT against radiolysis at nominal strength (62 mCi/mL) with or without the presence of oxygen. For these studies, very high concentrations of ascorbic acid were used (50 to 100 mg/mL). However, at slightly reduced concentrations of ascorbic acid (8 mg/mL) and higher [F-18]FLT strength (130 mCi/mL), ascorbic acid failed to stabilize [F-18]FLT with or without the presence of oxygen, suggesting that the amount of radiolysis was independent of oxygen. Ascorbic acid can stabilize [F-18]FLT against radiolysis, but only up to a mCi/mL concentration that is lower than that of oxygen sparged samples or samples containing oxygen plus maleic acid. Also, given that ascorbic acid is a reductant, any oxygen present in solution would be consumed by ascorbic acid, thus negating any stabilizing effect due to oxygen. In this experiment, ascorbic acid failed to provide radiolytic protection for [F-18]FLT beyond a strength of 130 mCi/mL.

| Entry | FLT Batch (MIBR) | Strength (mCi/mL) | Headspace (+/−) | AA (+/−) | Time | RCP |
|---|---|---|---|---|---|---|
| 1 | Dose vial | 62 | + | 50 mg/mL | 6 hrs | 100% |
| 2 | Syringe | 62 | + | 50 mg/mL | 6 hrs | 100% |
| 3 | Syringe | 62 | − | 50 mg/mL | 6 hrs | 100% |
| 4 | Dose Vial | 50 | + | 50 mg/mL | 7 hrs | 100% |
| 5 | Syringe | 50 | + | 50 mg/mL | 7 hrs | 100% |
| 6 | Syringe | 50 | − | 50 mg/mL | 7 hrs | 100% |
| 7 | Dose vial/syringe | 66 | + | 100 mg/mL | 4 hrs | 100% |
| 8 | Dose vial/syringe | 66 | − | 100 mg/mL | 4 hrs | 100% |
| 9 | Dose Vial | 130 | + | 8 mg/mL | 4.5 hrs | 82% |
| 10 | Dose Vial | 130 | − | 8 mg/mL | 4.5 hrs | 79% |

In addition to the processes described above, air may be incorporated into the above formulations be various means. One example involves simply placing the solution into a container (e.g., a sterile vial) that already has air in it in order to incorporate oxygen into the formulation. Another example involves using medical grade air push in order to place the solution into a container that already has air in it. Yet another example involves using medical grade air push to place both the solution and air into a container that does not have any air in it.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. A variety of modifications to the embodiments described will be apparent to those skilled in the art from the disclosure provided herein. Thus, the present invention may be embodied in other specific forms without departing from the spirit or essential attributes thereof. Various changes may be made without departing from the spirit and scope of the inventions as defined in the following claims.

Exemplary Embodiments

A first formulation for stabilizing a radiopharmaceutical, the first formulation including: a radiopharmaceutical, or a pharmaceutically acceptable salt thereof; a gas comprising oxygen; a stabilizer; and a solvent.

The first formulation, where water is the solvent.

The first formulation, where the stabilizer is an excipient compatible for human injection.

The first formulation, where the oxygen is present in the gas in an amount of at least about 10 vol. % by total volume of gas.

The first formulation, where the oxygen is present in an amount of about 10 vol. % to about 30 vol. % by total volume of gas.

The first formulation, where the oxygen is present in the gas in an amount of about 20.95 vol. % by total volume of gas.

The first formulation, further including an alcohol.

The first formulation, where the alcohol is ethanol.

The first formulation, where the ethanol is present in an amount of about 1.0 vol. % to about 10.0 vol. % per total volume of liquid.

The first formulation, wherein the ethanol is present in an amount of about 8.0 vol. % per total volume of liquid.

The first formulation, further including an inorganic salt.

The first formulation, where the inorganic salt is a phosphate.

The first formulation, where the aqueous phosphate solution is present in an amount of about 92 vol. % per total volume of liquid.

The first formulation, where the phosphate is about 21 mM sodium phosphate with a pH in a rage of 4.0 to 7.0.

The first formulation, where the radiopharmaceutical is [F-18]-FLT.

The first formulation, where the radiopharmaceutical is present in an amount of about 10.00 mCi/mL to about 1000.00 mCi/mL.

The first formulation, where the radiopharmaceutical is present in an amount of about 60 mCi/mL to about 200 mCi/mL.

The first formulation, where the stabilizer is maleic acid.

The first formulation, where the maleic acid is present in an amount of about 1 mg/10 mL.

The first formulation, further including sodium phosphate and about 0.01% maleic acid in grams of maleic acid per total volume of liquid in milliliters, where radiopharmaceutical is [F-18]-FLT.

A first apparatus for stabilizing a radiopharmaceutical, the first apparatus including a container with a formulation having a radiopharmaceutical (or a pharmaceutically acceptable salt thereof), a gas comprising oxygen, a stabilizer, and water.

The first apparatus, where the formulation comprises an aqueous solution.

The first apparatus, where the container is a vial.

The first apparatus, where the container is a syringe.

The first apparatus, where the container is sealable and when sealed, is substantially impervious to oxygen.

The first apparatus, further including a headspace between a boundary of the formula and a boundary of the container, wherein the headspace is substantially filled with the oxygen.

The first apparatus, where the formula further comprises ethanol.

The first apparatus, where the ethanol is at concentrations of about 1.0 vol. % to about 10.0 vol. % per total volume of liquid.

The first apparatus, where the oxygen is present in an amount of about 10 vol. % to about 100 vol. % per total volume of gas.

The first apparatus, where the oxygen is present in an amount of about 20.95 vol. % per total volume of gas.

The first apparatus, where the ethanol is present in an amount of about 8.0 vol. % per total volume of liquid.

The first apparatus, where the formula further comprises aqueous phosphate in an amount of about 92 vol. % per total volume of liquid.

The first apparatus, where the radiopharmaceutical is [F-18]FLT.

The first apparatus, where the radiopharmaceutical is present in an amount of about 10.0 mCi/mL to about 1000.0 mCi/mL.

The first apparatus, where the radiopharmaceutical is present in an amount of about 60.0 mCi/mL to about 200.00 mCi/mL.

The first apparatus, where the stabilizer is maleic acid.

A first method of making a formulation for stabilizing a radiopharmaceutical, the first method including providing a radiopharmaceutical, providing an excipient, providing an aqueous solution of an alcohol and an inorganic salt, and providing oxygen.

The first method, where an amount of excipient provided is about 0.001 to about 100 mg/mL.

The first method, where the excipient is selected from the group consisting of maleic acid, beta-cyclodextrin, methylene blue, alpha-cyclodextrin, gentisic acid, cyclohexane dione diamine, thioglycerol, glutathione, tartaric acid, niacinamide, $FeCl_3$, $H_2O_2$, glutamic acid, triamine pentaacid, methylene diphosphonic acid, beta-hydroxypropyl cyclodextrin, xanthine, aspartic acid, chlorobutanol, calcium chloride, mannitol, creatanine, calcium gluconate, dimethyl acetamide, diazatriazoic acid, sodium succinate, boric acid, sodium carbonate, acetic acid, and acetates.

The first method, where the excipient is maleic acid.

A second method of making a formulation for stabilizing a radiopharmaceutical, the second method including: providing a sterile container filled with air; providing a formulation having a radiopharmaceutical (or a pharmaceutically acceptable salt thereof), an stabilizer, and a solvent; and placing the formulation in the sterile container.

The second method, where the formulation is placed in the sterile container by medical grade air push.

The second method, where the solvent is water.

The second method, where the stabilizer is an excipient.

The second method, where an amount of excipient provided is about 0.001 to about 100 mg/mL.

The second method, where the excipient is selected from the group consisting of maleic acid, fumaric acid, beta-cyclodextrin, methylene blue, alpha-cyclodextrin, gentisic acid, cyclohexane dione diamine, thioglycerol, glutathione, tartaric acid, niacinamide, $FeCl_3$, $H_2O_2$, glutamic acid, triamine pentaacid, methylene diphosphonic acid, beta-hydroxypropyl cyclodextrin, xanthine, aspartic acid, chlorobutanol, calcium chloride, mannitol, creatanine, calcium gluconate, dimethyl acetamide, diazatriazoic acid, sodium succinate, boric acid, sodium carbonate, acetic acid, and acetates as well as isomers thereof.

The second method, where the excipient is maleic acid.

The second method, where the sterile container is a sterile vial.

The second method, where the sterile container is a sterile syringe.

The second method, where the sterile container is sealable and when sealed, is substantially impervious to oxygen.

A third method of making a formulation for stabilizing a radiopharmaceutical, the method including: providing a sterile container; providing a formulation having a radiopharmaceutical (or a pharmaceutically acceptable salt thereof), a stabilizer, and a solvent; and placing the formulation in the sterile container by medical grade air push.

The third method, where there is no air in the sterile container before the formulation is placed in the sterile container.

The third method, where the solvent is water.

The third method, where the stabilizer is an excipient.

The third method, where an amount of excipient provided is about 0.001 to about 100 mg/mL.

The third method, where the excipient is selected from the group consisting of maleic acid, fumaric acid, beta-cyclodextrin, methylene blue, alpha-cyclodextrin, gentisic acid, cyclohexane dione diamine, thioglycerol, glutathione, tartaric acid, niacinamide, $FeCl_3$, $H_2O_2$, glutamic acid, triamine pentaacid, methylene diphosphonic acid, beta-hydroxypropyl cyclodextrin, xanthine, aspartic acid, chlorobutanol, calcium chloride, mannitol, creatanine, calcium gluconate, dimethyl acetamide, diazatriazoic acid, sodium succinate, boric acid, sodium carbonate, acetic acid, and acetates.

The third method, where the excipient is maleic acid.

The third method, where the sterile container is a sterile vial.

The third method, where the sterile container is a sterile syringe.

The third method, where the sterile container is sealable and when sealed, is substantially impervious to oxygen.

A first kit including a container with a formulation having a radiopharmaceutical (or a pharmaceutically acceptable salt thereof), a gas comprising oxygen, a stabilizer, and a solvent.

The first kit, where the solvent is water.

The first kit, where the formulation comprises an aqueous solution.

The first kit, where the container is a vial.

The first kit, where the container is a syringe.

The first kit, where the container is sealable and when sealed, is substantially impervious to oxygen.

The first kit, further including a headspace between a boundary of the formula and a boundary of the container, wherein the headspace is substantially filled with the oxygen.

The first kit, where the formula further comprises ethanol.

The first kit, where the ethanol is at concentrations of about 1.0 vol. % to about 10.0 vol. % per total volume of liquid.

The first kit, where the oxygen is present in an amount of about 5 vol. % to about 100 vol. % per total volume of gas.

The first kit, where the oxygen is present in an amount of about 20.95 vol. % per total volume of gas.

The first kit, where the ethanol is present in an amount of about 8.0 vol. % per total volume of liquid.

The first kit, where the formula further comprises aqueous phosphate in an amount of about 92 vol. % per total volume of liquid.

The first kit, where the radiopharmaceutical is [F-18]FLT.

The first kit, where the radiopharmaceutical is present in an amount of about 10.0 mCi/mL to about 1000.0 mCi/mL.

The first kit, where the radiopharmaceutical is present in an amount of about 60.0 mCi/mL to about 200.00 mCi/mL.

The first kit, where the stabilizer is maleic acid.

What is claimed is:

1. A formulation for stabilizing a radiopharmaceutical, the formulation comprising:
   a F-18 labelled radiopharmaceutical, or a pharmaceutically acceptable salt of a F-18 labelled radiopharmaceutical thereof;
   a gas comprising oxygen; wherein the oxygen is present in the gas in an amount of at least about 10 vol. % by total volume of gas; and where the gas is disposed in a headspace of a vial containing the F-18 labelled radiopharmaceutical or the pharmaceutically acceptable salt of the F-18 labelled radiopharmaceutical stabilizer, wherein the stabilizer is maleic acid; and
   an alcohol.

2. The formulation of claim 1; further comprising a solvent; wherein water is the solvent.

3. The formulation of claim 1, further comprising:
   an inorganic salt.

4. The formulation of claim 1, where the alcohol is present in an amount of about 1 volume percent to 10 volume percent based on the total volume of liquid.

* * * * *